(12) United States Patent
Li et al.

(10) Patent No.: US 11,623,216 B2
(45) Date of Patent: Apr. 11, 2023

(54) SAMPLE TESTING APPARATUS, MANUFACTURING METHOD THEREOF, AND SAMPLE TESTING METHOD

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Tiansheng Li, Beijing (CN); Zhenyu Xie, Beijing (CN); Lijun Mao, Beijing (CN)

(73) Assignees: Beijing Boe Optoelectronics Technology Co., Ltd., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 582 days.

(21) Appl. No.: 16/318,116

(22) PCT Filed: May 17, 2018

(86) PCT No.: PCT/CN2018/087303
§ 371 (c)(1),
(2) Date: Jan. 15, 2019

(87) PCT Pub. No.: WO2019/041893
PCT Pub. Date: Mar. 7, 2019

(65) Prior Publication Data
US 2019/0232280 A1    Aug. 1, 2019

(30) Foreign Application Priority Data

Sep. 1, 2017  (CN) .......................... 201710778797.1

(51) Int. Cl.
*B01L 3/00*        (2006.01)
*G01N 33/52*       (2006.01)
(Continued)

(52) U.S. Cl.
CPC ... *B01L 3/502707* (2013.01); *B01L 3/502715* (2013.01); *C12M 1/34* (2013.01);
(Continued)

(58) Field of Classification Search
CPC ......... B01L 3/502707; B01L 3/502715; G01N 33/521; G01N 33/526; H01L 23/538; H01L 23/31; C12M 1/34
See application file for complete search history.

(56) References Cited

U.S. PATENT DOCUMENTS

2004/0110277 A1   6/2004  Maeda
2005/0045889 A1*  3/2005  Fryer ..................... H01L 27/12
                                                  257/72

(Continued)

FOREIGN PATENT DOCUMENTS

EP          0235153 B1    6/1991

OTHER PUBLICATIONS

International Search Report and Written Opinion dated Aug. 20, 2018 in PCT/CN2018/087303.

(Continued)

*Primary Examiner* — William H. Beisner
*Assistant Examiner* — Danielle B Henkel
(74) *Attorney, Agent, or Firm* — Syncoda LLC; Feng Ma

(57) ABSTRACT

A sample testing apparatus for characterizing at least one target molecule in a testing sample includes a substrate and at least one detection device over the substrate. Each detection device includes a plurality of electrodes, a plurality of data lines, and a probe. Each electrode is configured, upon reaction of the probe with one of the at least one target molecule, to sense an electrical signal, and then to transmit the electrical signal via the one data line. Each data line includes a first film layer and at least one other film layer disposed over the first film layer. The first film layer can be (Continued)

at a substantially same layer, and have a first composition substantially same, as the electrodes. One or more of the at least one other film layer can have a composition having a relatively lower electric resistance than the first composition.

12 Claims, 12 Drawing Sheets

(51) Int. Cl.
      *H01L 23/538*     (2006.01)
      *H01L 23/31*      (2006.01)
      *C12M 1/34*      (2006.01)

(52) U.S. Cl.
    CPC ......... *G01N 33/521* (2013.01); *G01N 33/526* (2013.01); *H01L 23/31* (2013.01); *H01L 23/538* (2013.01)

(56) References Cited

U.S. PATENT DOCUMENTS

| | | |
|---|---|---|
| 2010/0170792 A1 | 7/2010 | Lin et al. |
| 2010/0216267 A1* | 8/2010 | Cho .................... H01L 51/0545 438/34 |
| 2014/0154859 A1* | 6/2014 | Gopal .................. H01L 45/145 438/382 |
| 2017/0102350 A1 | 4/2017 | Lu |

OTHER PUBLICATIONS

Extended European Search Report (EESR) dated Jul. 22, 2021 in EP 18796813.6.

* cited by examiner

SAMPLE TESTING APPARATUS, MANUFACTURING METHOD THEREOF, AND SAMPLE TESTING METHOD

CROSS-REFERENCE TO RELATED APPLICATION

The present application claims priority to Chinese Patent Application No. 201710778797.1 filed on Sep. 1, 2017, the disclosure of which is hereby incorporated by reference in its entirety.

TECHNICAL FIELD

The present disclosure relates generally to the field of sample testing technologies, and more specifically to a sample testing apparatus, its manufacturing method, and a sample testing method using the sample testing apparatus.

BACKGROUND

With the rapid development of the genetic testing technologies in recent years, the genetic testing market has increased from $7.94 million in 2007 to about $4.5 billion in 2013, with a compound growth rate of 33.5%. It is expected that the trend of rapid growth will remain in the next few years.

The cost of a whole-genome sequencing for the human genome was about $3 billion when the human genome project was completed in 2001, while the cost has dropped to around $1 million in 2007, and further dropped to less than $1,000 in January 2014. According to a prediction by McCauley, the cost of the whole-genome sequencing may be less than $100 in a couple of years, and by 2020, the cost of sequencing the human genome may cost only $1.

Yet so far, the cost for sequencing a whole human genome is still at a level that is not broadly accepted, and the popularity of sequencing for genes implicated in some of the major diseases is also relatively low. As such, a market-acceptable genetic testing for genes implicated in mainstream diseases, such as in major cancers, is in urgent needs and has been actively pursued by all players and companies in the market.

The birth of the technology of liquid biopsy chips, has marked one major milestone in the above major pursuit. The technology of liquid biopsy chips is capable of detecting human diseases without the need to screen the whole genome, and can be utilized for the detection and analysis based directly on a certain amount of human body fluids that have been directly collected from a human subject.

For example, the presence of lung cancer, liver cancer, and several other common human cancers, can be detected by liquid biopsy chips-depending genetic testing analysis over multiple disease-associated genes based only on a small volume human blood samples from a human subject, or even a small volume of saliva or sweat samples collected noninvasively from the human subject.

The liquid biopsy chip-based genetic testing technology also has an advantage that it requires no expensive equipments, and can be utilized for a diagnosis based on changes in an electric signal on an electrode in a sample testing apparatus. At present, the accuracy of diagnosis for the technology can reach above 95%.

SUMMARY

In a first aspect, the present disclosure provides a sample testing apparatus, which can be used for characterizing at least one target molecule in a testing sample.

The sample testing apparatus comprises a substrate and at least one detection device over the substrate. Each of the at least one detection device comprises a plurality of electrodes, a plurality of data lines, and a probe configured to react with one of the at least one target molecule.

Each of the plurality of data lines includes a plurality of film layers. Each of the plurality of electrodes is electrically coupled to one of the plurality of data lines. Each of the plurality of electrodes is configured, upon reaction of the probe with the one of the at least one target molecule, to sense an electrical signal, and then to transmit the electrical signal via the one of the plurality of data lines.

In each of the at least one detection device in the sample testing apparatus, each of the plurality of data lines can comprise a first film layer, which is configured to be at a substantially same layer as the plurality of electrodes.

Herein the first film layer can have a first composition substantially same as the plurality of electrodes, wherein the first composition is compatible with the testing sample. The first composition can be a noble metal, such as gold (Au), silver (Ag) and platinum (Pt), etc.

In the sample testing apparatus disclosed herein, in each of the at least one detection device, each of the plurality of data lines can further comprise at least one other film layer, which is disposed over a side of the first film layer distal to the substrate.

Herein one or more of the at least one other film layer can be configured to have a composition having a relatively lower electric resistance than the first composition.

According to some embodiments of the sample testing apparatus, the at least one other film layer comprises a second film layer over the side of the first film layer distal to the substrate, an insulating layer is sandwiched between the first film layer and the second film layer, and the second film layer is electrically coupled with the first film layer through a via in the insulating layer.

In the sample testing apparatus disclosed herein, in each of the at least one detection device, the plurality of electrodes can be grouped into at least one subset of electrodes, and each of the at least one subset of electrodes can be electrically coupled to a same data line.

According to some specific embodiments of the sample testing apparatus, the plurality of data lines can comprise a first data line and a second data line, and the plurality of electrodes can be grouped into two subsets of electrodes, which are electrically coupled to the first data line and the second data line respectively.

In the sample testing apparatus, in each of the at least one detection device, the plurality of electrodes can be arranged in a matrix having a plurality of rows. Electrodes in each of the plurality of rows can be connected to one another in series. One of the two subsets of electrodes can comprise electrodes in odd-number rows, and another of the two subsets of electrodes can comprise electrodes in even-number rows.

In the sample testing apparatus disclosed herein, each of the at least one detection device can further comprise a packaging portion, which encircles the plurality of electrodes to thereby form an accommodation space for the testing sample.

Within the accommodation space, each of the at least one detection device can further comprise a conductive layer over a side of the plurality of electrodes distal to the substrate and a probe base layer over a side of the conductive layer distal to the substrate. The probe base layer is configured to provide a surface for attaching or growing molecules of the probe thereon.

According to some embodiments of the sample testing apparatus described above, each of the conductive layer and the probe base layer has a substantially same pattern as the plurality of electrodes.

In a second aspect, the present disclosure further provides a method for manufacturing a sample testing apparatus (i.e. manufacturing method).

The manufacturing method comprises the following steps of:

providing a substrate; and forming at least one detection device over the substrate;

It is configured such that each of the at least one detection device comprises a plurality of electrodes, a plurality of data lines, and a probe configured to react with one target molecule in a testing sample. Each of the plurality of data lines comprises a plurality of film layers. Each of the plurality of electrodes is electrically coupled to one of the plurality of data lines, and is configured, upon reaction of the probe with the one target molecule, to sense, and to transmit via the one of the plurality of data lines, an electrical signal.

According to some embodiments of the method, each of the plurality of data lines in each of the at least one detection device includes a first film layer and at least one other film layer disposed over one another over a side of the first film layer distal to the substrate. The first film layer is arranged at a layer substantially same, and configured to have a first composition substantially same, as the plurality of electrodes. One or more of the at least one other film layer has a composition having a relatively lower electric resistance than the first composition.

In the method described above, the step of forming at least one detection device over the substrate comprises the following sub-steps:

forming the plurality of electrodes and the first film layer of each of the plurality of data lines over the substrate; and forming the at least one other film layer of the each of the plurality of data lines over a side of the first film layer distal to the substrate.

Herein, the sub-step of forming the plurality of electrodes and the first film layer of each of the plurality of data lines over the substrate can be performed by using a single mask.

The at least one other film layer can include a second film layer, configured to have a second composition having a relatively lower electric resistance than the first composition. As such, the sub-step of forming the at least one other film layer of the each of the plurality of data lines over a side of the first film layer distal to the substrate comprises:

forming the second film layer of the each of the plurality of data lines over the side of the first film layer distal to the substrate.

According to some embodiments of the method described above, the sub-step of forming the second film layer of the each of the plurality of data lines over the side of the first film layer distal to the substrate comprises:

forming an insulating layer over the plurality of electrodes and the first film layer of the each of the plurality of data lines;

treating the insulating layer such that each of the plurality of electrodes is exposed and at least one via is formed in the insulating layer; and forming the second film layer over the insulating layer such that the second film layer is electrically connected with the first film layer through the at least one via.

Herein the treating the insulating layer such that each of the plurality of electrodes is exposed and at least one via is formed in the insulating layer can be performed by using a single mask.

According to some other embodiments of the method, the forming the second film layer of the each of the plurality of data lines over the side of the first film layer distal to the substrate comprises:

forming the second film layer on the first film layer such that the second film layer is directly stacked on the side of the first film layer distal to the substrate.

In the method, the step of forming at least one detection device over the substrate can further include the following sub-steps:

forming a conductive layer over a side of the plurality of electrodes distal to the substrate;

forming a probe base layer over a side of the conductive layer distal to the substrate; and forming the probe on a surface of the probe base layer distal to the substrate;

Herein the step of forming at least one detection device over the substrate can further comprise:

forming a packaging portion over the substrate, such that the package portion encircles the plurality of electrodes to thereby form an accommodation space for the testing sample.

DETAILED DESCRIPTION

In the following, with reference to the drawings of various embodiments disclosed herein, the technical solutions of the embodiments of the disclosure will be described in a clear and fully understandable way.

It is obvious that the described embodiments are merely a portion but not all of the embodiments of the disclosure. Based on the described embodiments of the disclosure, those ordinarily skilled in the art can obtain other embodiment(s), which come(s) within the scope sought for protection by the disclosure.

In existing sample testing chips such as a genetic testing chip, or a DNA testing chip, each of the data lines used to collect electric signals typically comprises a one-layer metal, and because of such a structure, the data lines usually have a high electric resistance, which commonly leads to a high testing noise during normal sample testing analysis. The high testing noise has significantly limited the wide application of the technology utilizing the sample testing chips. Therefore, how to reduce the testing noise of a gene detection chip has become a technical issue that needs to be urgently solved in this field.

In light of this above technical issue associated with existing sample testing apparatus, the present disclosure provides a sample testing apparatus, its manufacturing method, and a sample testing method using the sample testing apparatus.

In a first aspect, the present disclosure provides a sample testing apparatus.

Figure 1:
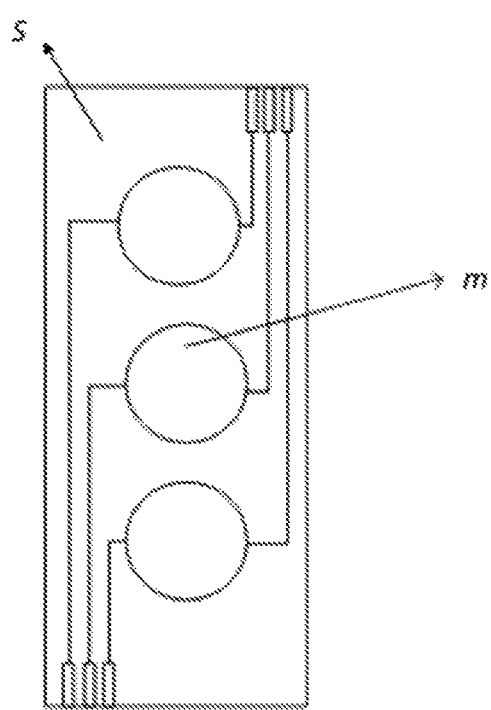
FIG. 1 illustrates a schematic diagram of a sample testing apparatus according to some embodiments of the present disclosure.

FIG. 1 illustrates a schematic diagram of a sample testing apparatus according to some embodiments of the present disclosure. As shown in the figure, the sample testing apparatus includes a plurality of detection devices m, arranged over a substrate s.

Figure 2:
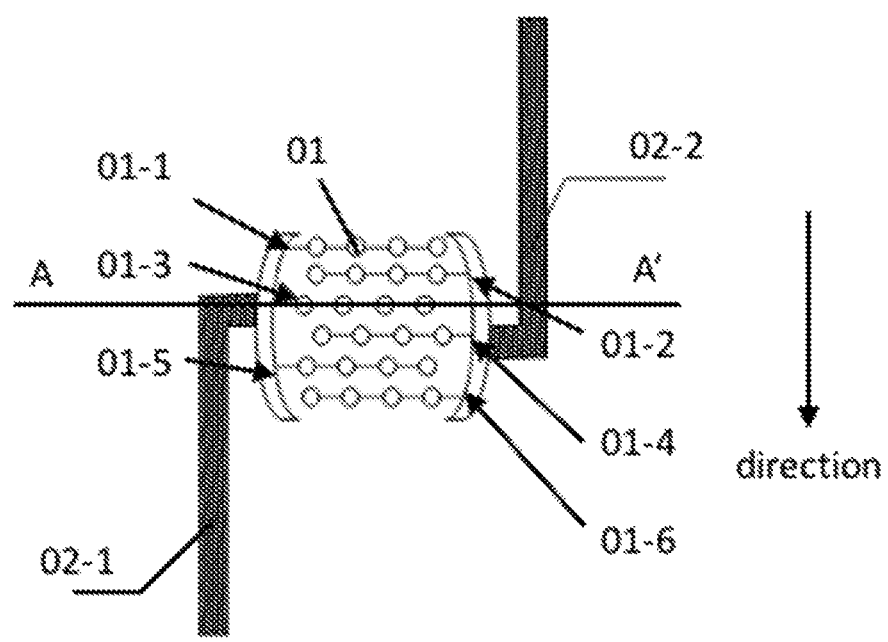
FIG. 2 illustrates a detection device of the sample testing apparatus as illustrated in FIG. 1.

In the sample testing apparatus, each of the plurality of detection devices m is substantially a sample detection unit that includes a plurality of electrodes 01, and a plurality of data lines 02 electrically coupled to each of the plurality of electrodes 01, as illustrated in FIG. 2.

The plurality of electrodes 01 are configured to have a composition of a conductive material having a relatively good compatibility with the sample to be tested. Herein the good compatibility with the sample to be tested is defined as a characteristics of a material, such as the conductive material used for the plurality of electrodes 01, that the material itself does not interfere with the reactions of molecules in the sample to be tested with the probes in each detection device (e.g. not prone for any physical or chemical reactions that may interfere) or with the detection of electrical signals obtained from each of the plurality of electrodes 01 and transmitted via the plurality of data lines 02.

Examples of some commonly used conductive material can be a noble metal, such as gold (Au), silver (Ag) and platinum (Pt), etc. It should be noted that the conductive material can also be another metal, an alloy, or even a non-metal conductive material as long as it meets the requirement that it has a relatively good compatibility with the sample to be tested.

Each of the plurality of detection devices comprises a probe that is configured to specifically characterize a target molecule in a testing sample. Herein the characterization of the target molecule can include a qualification, and/or quantification of the target molecule in the testing sample.

The probe and the target molecule substantially form a corresponding pair of reacting partners, which can be a pair of binding partners including a DNA-DNA pair, a DNA-RNA pair, a RNA-DNA pair, an antibody-antigen pair, an antigen-antibody pair, a biotin-streptavidin pair, etc., but can also be a pair of reactants in a chemical reaction.

According to some embodiments, the probes 05 in a detection device of the sample testing apparatus are a plurality of oligo nucleotides with a first sequence, which can hybridize specifically with target nucleic acid molecules (e.g. DNA or RNA) having a second sequence complimentary to the first sequence of the probes. These above embodiments of the sample testing apparatus can be particularly useful for a DNA sequencing array.

According to some other embodiments, the probes in a detection device of the sample testing apparatus are a plurality of antibodies, and the target molecules in the testing sample can have an epitope that can be specifically bound by the antibodies.

In the specific embodiments of the sample testing apparatus as illustrated in FIG. 2, the plurality of electrodes 01 in each detection device m are arranged in a matrix, and each electrode 01 is of a shape of a circle. Two data lines 02 (i.e. a first data line 02-1 and a second data line 02-2) are respectively arranged on two opposing sides of each detection device m and are electrically coupled to each of the plurality of electrodes 01.

The plurality of electrodes 01 in each detection device m are further grouped into a plurality of subsets. The electrodes 01 in each subset are electrically connected to one another in series, and are all configured to be electrically coupled to one same data line 02 (i.e. 02-1 or 02-2).

In the specific embodiment of the detection device as shown in FIG. 2, the plurality of electrodes 01 in each detection device m are grouped into subsets based on rows, and each row of electrodes 01 substantially form a subset of electrodes. It is configured such that a first subset of electrodes having an odd row number (01-1, 01-3, 01-5, . . . ) are electrically coupled to a first data line 02-1, and a second subset of electrodes having an even row number (01-2, 01-4, 01-6, . . . ) are electrically coupled to a second data line 02-2. In FIG. 2, it is noted that the row number increases according to the counting direction from top to bottom, as shown by the upright arrow in the figure.

It is noted that the above configuration of electrodes and data lines for the detection devices serves as an illustrating example only, and shall not be interpreted as a limitation to the scope of the disclosure. Other embodiments for the arrangement of electrodes 01 and data lines 02 are also possible. For example, each electrode 01 can be of a shape other than a circle, which can be a squire, a triangle, a rectangle, or any other shape depending on practical needs and specific design. The plurality of electrodes 01 can be arranged in an array of strip-shaped electrodes (i.e. array of electrode strips, not shown in the drawings). The specific grouping of electrodes 01 and the electrical coupling between each electrode 01 and each data line 02 can take any configuration.

In the sample testing apparatus disclosed herein, each of the plurality of data lines is configured to have a relatively low electrical resistance, which can reduce the testing noise during normal sample testing analysis compared with conventional design where each data line has only one-layer of metal. As such, each data line can be configured to have a special composition, and/or a special structure, to thereby realize that it has a relatively low electrical resistance.

According to some embodiments, each data line substantially comprises a multilayer structure having a plurality of film layers, thereby causing each data line to have a reduced electrical resistance compared with otherwise. Specifically, the multilayer structure for each data line comprises a first film layer over the substrate, and at least one other film layer over the first film layer.

Optionally, the first film layer of each data line can be configured to be at a substantially same layer as the plurality of electrodes. Furthermore, the first film layer of each data line can be additionally configured to have a substantially same composition as the plurality of electrodes (i.e. the aforementioned conductive material). In other words, according to some embodiments, the first film layer can be configured to be at a substantially same or different layer as, and have a substantially same or different composition as, the plurality of electrodes.

It is noted that there is no limitation to the relative position and composition of the first film layer, or to the relatively arrangement of, and/or to the composition of, each of the at least one other film layer, as long the multilayer structure composed of the first film layer and the at least one other film layer has a relatively low electrical resistance.

Figure 3A:
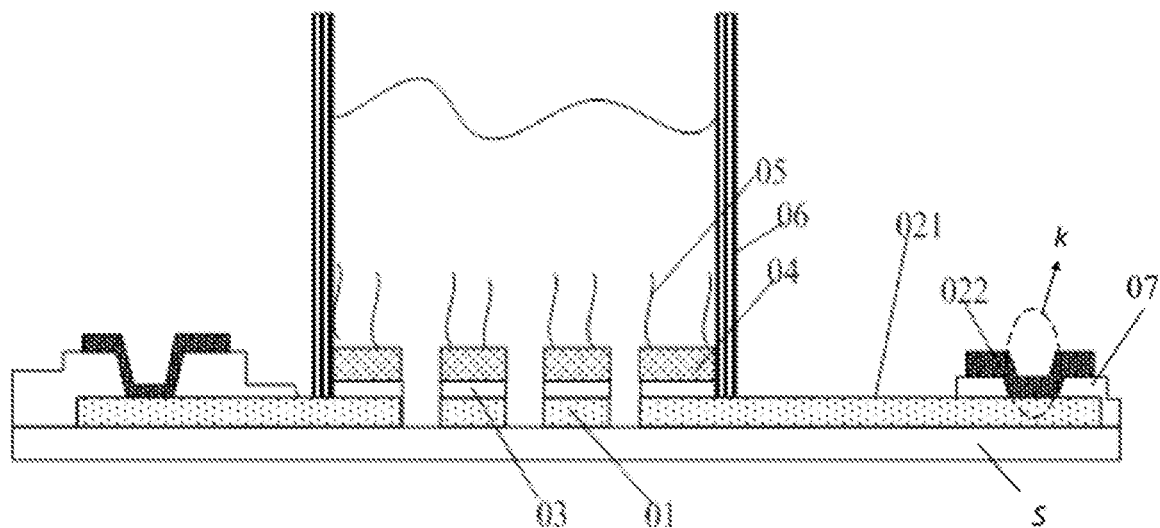
FIG. 3A is a cross-sectional view of a detection device of the sample testing apparatus as illustrated in FIG. 2 along the line A-A'.

FIG. 3A illustrates a cross-sectional view of the detection device of the sample testing apparatus as shown in FIG. 2 along the line A-A' according to some embodiments of the disclosure. As shown in the figure, the multilayer structure of each data line 02 substantially comprises a first film layer 021 and a second film layer 022. The first film layer 021 is disposed over the substrate s, and the second film layer 022 is disposed over the first film layer 021. An insulating layer 07 is disposed between the first film layer 021 and the second film layer 022, and the second film layer 022 is electrically coupled or connected to the first film layer 021 through a via k (as shown by the circle with dotted line in FIG. 3A). The first film layer 021 has a first composition, and the second film layer 022 has a second composition. The first composition and/or the second composition can be a metal, an alloy, or other conductive material.

Further as illustrated in FIG. 3A, the first film layer 021 of each data line 02 is configured to be at a substantially same layer as the plurality of electrodes 01. According to some embodiments, the first film layer 021 of each data line 02 can have a substantially same composition as the plurality of electrodes 01. As such, the conductive material can be a noble metal, such as gold (Au), silver (Ag) and platinum (Pt), etc.

By the above configuration (i.e., the first film layer 021 of each data line 02 is at a substantially same layer as the plurality of electrodes 01, and has a composition that is substantially same as the conductive material used for the plurality of electrodes 01), the first layer 021 of each data line 02 and the plurality of electrodes in each detection device can be manufactured by a substantially same process, for example, a patterning process. In addition, the conductive material has a relatively good compatibility with the testing sample, allowing the sample testing to be carried out without the unwanted interference.

In the embodiment as shown in FIG. 3A, the second composition for the second film layer 022 can be same or different as the first composition used for the first film layer 021. Regardless of the same or different composition, the first film layer 021 and the second film layer 022 substantially form a parallel electrical connection, resulting in a reduced electrical resistance.

According to some embodiments, the second composition can be further configured to have a relatively lower electric resistance than the first composition used for the first film layer 021. As such, the electric resistance of the data line 02 can be further reduced, in turn leading to a further reduced testing noise of the sample testing apparatus.

It is noted that in each data line 02, the at least one other film layer over the first film layer 021 can further comprise film layers in addition to the second film layer 022 (not shown in the drawings), such as a third film layer, a fourth film layer, etc. Each of these other film layers can have a composition that is same as, or different from, the composition for the first film layer 021 or for the second film layer 022, as long as the multilayer data line as a whole has a reduced electric resistance. Preferably, each of these other film layers can have a composition having a relatively lower electric resistance than the first composition used for the first film layer 021.

To manufacture the plurality of data lines 02 having the above configuration (i.e. each data line 02 has a first film layer 021 and at least one other film layer, such as a second film layer 022), a manufacturing process of several rounds of superposition or of several rounds of mask preparation can be applied.

As such, in each of the plurality of data lines 02 being manufactured thereby, a first portion thereof that is at a substantially same layer as the plurality of electrodes 01 can be configured to have a substantially same composition as the plurality of electrodes 01, and a second portion thereof that is over the first portion can be configured to have at least one metal film layer over the first portion, each configured to have a composition of a relatively lower electric resistance. Such a configuration allows the plurality of electrodes 01 to be relatively compatible with the genetic materials to be tested, and also reduces the electric resistance of each of the plurality of data lines 02.

It is noted that in addition to the above embodiment as illustrated in FIG. 3 A, the second film layer 022 can be stacked directly over the first film layer 021 without an insulating layer 07 and the via k arranged therein, and other arrangements are also possible. Similarly, the arrangement of the at least one other film layers over the first film layer 021 can have different manners, depending on the practical needs.

Further as illustrated in FIG. 3A, the embodiment of a detection device of the sample testing apparatus further comprises a conductive layer 03 and a probe base layer 04. The conductive layer 03 is disposed over each electrode 01, and the probe base layer 04 is disposed over the conductive layer 03. The probe base layer 04 is configured to provide a surface for attaching or growing probes 05, and the probes 05 are configured to specifically react with target molecules in the testing sample, and the electrodes 01 can, upon the specific reaction of the target molecules with the probes 05 on the probe base layer 04, generate an electrical signal which can be transmitted through the data line 02 to be detected and analyzed.

In order to realize a detection of target molecules in a testing sample, each detection device of the sample testing apparatus further comprises a packaging portion 06, which is configured to package the plurality of electrodes 01 to thereby form an accommodation space for accommodating the sample to be tested (i.e. testing sample). The accommodating space is substantially a reaction and detection space for each detection device of the sample testing apparatus, where the testing sample can be loaded, be allowed to react with the probes 05, and be qualitatively and/or quantitatively analyzed for the specific reaction via the electrical signals from the plurality of electrodes 01 and transmitted through the plurality of data lines 02.

In this embodiment of the detection device of the sample testing apparatus described herein and illustrated in FIG. 3A, within the accommodation space that is defined by the packaging portion 06, each of the conductive layer 03 and the probe base layer 04 has a pattern that is substantially same as the pattern of the plurality of electrodes 01.

It is noted that in addition to the embodiment of the detection device of the sample testing apparatus described above and illustrated in FIG. 3A, other embodiments of the detection device of the sample testing apparatus are also possible.

Figure 3B:
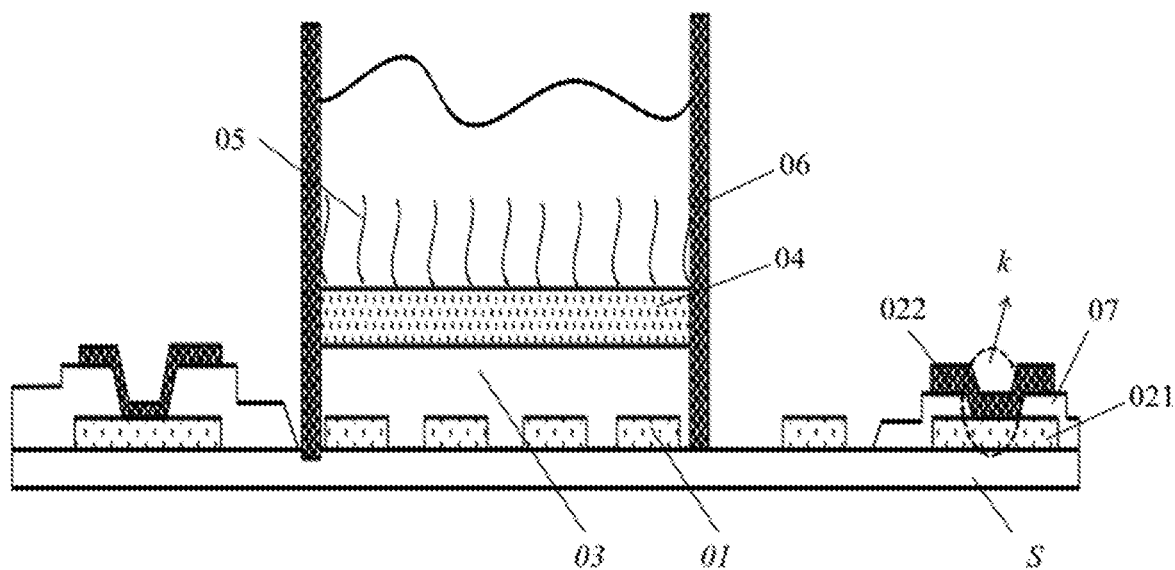
FIG. 3B is a cross-sectional view of a detection device of the sample testing apparatus as illustrated in FIG. 2 along the line A-A' according to yet another embodiment of the disclosure.

For example, in yet another embodiment of the detection device of the sample testing apparatus as illustrated in FIG. 3B, the detection device also includes a conductive layer 03, a probe base layer 04, and probes 05, sequentially disposed over the plurality of electrodes 01, and the detection device further includes an accommodation space defined by the packaging portion 06.

Yet there is at least one feature of the embodiment shown in FIG. 3B that differs from the embodiment as illustrated in FIG. 3A: each of the conductive layer 03 and the probe base layer 04 has a pattern that is substantially different from the pattern of the plurality of electrodes 01. Specifically, in the embodiment of the detection device as illustrated in FIG. 3B, each of the conductive layer 03 and the probe base layer 04 has substantially an integrated layer.

It is noted that the sample testing apparatus can include more than one detection device. Each of the more than one detection device can be provided with one different probe that is configured to specifically test one different target molecule in the testing sample in the sample testing analysis utilizing the sample testing apparatus. As such, the sample testing apparatus can realize a simultaneous detection of more than one target molecules in the testing sample, resulting in an elevated throughput and an increased efficiency. The more than one detection device can be arranged in a matrix over the substrate, but can have other arrangements.

In the embodiments of the sample testing apparatus as described above, each of the plurality of data line 02 is configured to have a multilayer structure which comprises a plurality of film layers. The first film layer 021 in each data line can be configured to have a substantially same composition, and be arranged at a substantially same layer, as the plurality of electrodes 01. As such, in addition that the compatibility of the plurality of electrodes 01 with the genetic materials to be tested can be guaranteed, the electric resistance of the data line can be reduced, which in turn can reduce the noise (i.e. the testing noise as mentioned above) during a sample testing process utilizing the sample testing apparatus.

In a second aspect, the present disclosure further provides a method for manufacturing the sample testing apparatus as described above.

Specifically, the manufacturing method comprises:

S100: Forming a plurality of detection devices over a substrate.

Herein each of the plurality of detection devices can be referenced to the various embodiments of the detection device as described above. Specifically, each detection device can comprise a plurality of electrodes and a plurality of data lines electrically coupled to each electrode.

The plurality of electrodes can be grouped into a plurality of subsets, and each electrode in each subset is configured to be electrically coupled to a same data line. Each data line has a multilayer structure. A first film layer in each data line is configured to be at a substantially same layer, and have a substantially same composition, as the plurality of electrodes. A conductive material having a relatively good compatibility with the testing sample can be used as the composition for the plurality of electrodes and for the first film layer of each data line. At least one another film layers other than the first film layer is configured to have a composition having a relatively lower electric resistance than the conductive material to thereby result in a reduced electric resistance for each data line.

In the sample testing apparatus manufactured by the method as described above, the plurality of electrodes are configured to be relatively compatible with the genetic materials to be tested, and the electric resistance of each of the plurality of data lines can also be reduced, leading to a reduced noise during testing.

Figure 4:
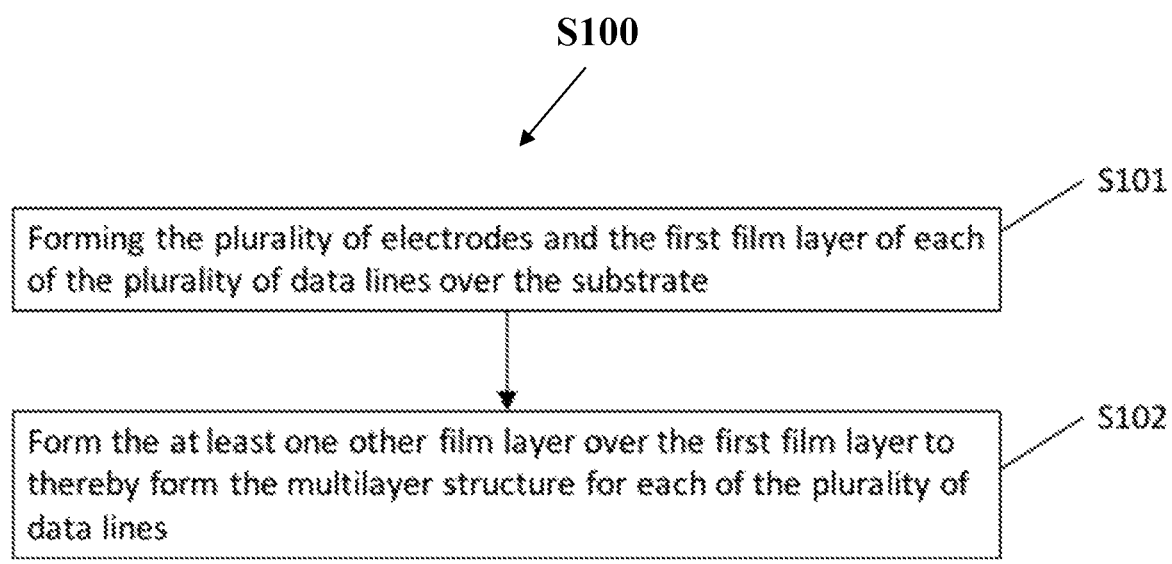
FIG. 4 illustrates a flow chart of fabricating data lines of a sample testing apparatus according to some embodiments of the present disclosure.
Figure 5A:
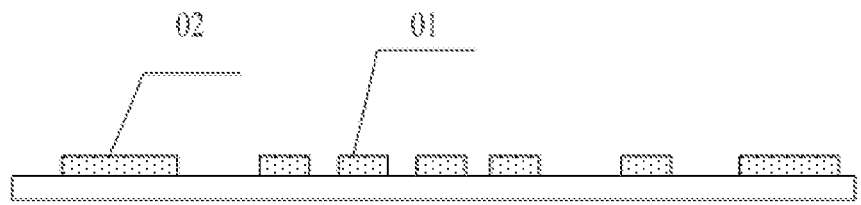
FIG. 5A, FIG. 5B, and FIG. 5C respectively illustrate a sample testing apparatus during various steps of a method for manufacturing a sample testing apparatus according to some embodiments of the present disclosure.
Figure 5B:
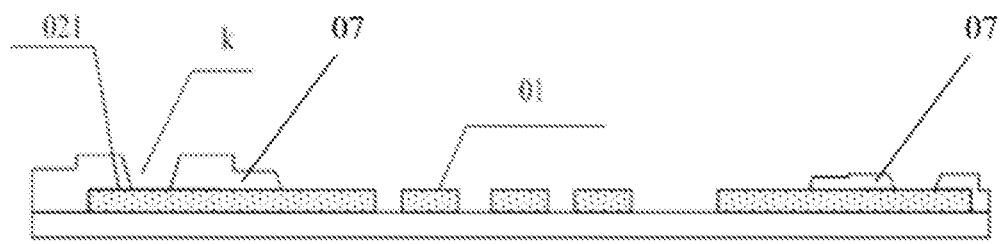
Figure 5C:
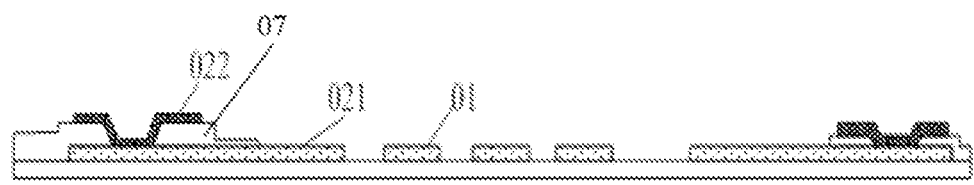

FIG. 4 illustrates a flow chart of a method for manufacturing a sample testing apparatus according to some embodiments of the present disclosure; and FIG. 5A, FIG. 5B, and FIG. 5C respectively illustrate a sample testing apparatus being manufactured during various steps of the manufacturing method of the sample testing apparatus;

As illustrated in FIG. 4, in the manufacturing method, the step S100 of forming a plurality of detection devices over a substrate can comprise the following sub-steps:

S101: Forming the plurality of electrodes 01 and the first film layer 021 of each of the plurality of data lines over the substrate; and S102: Form the at least one other film layer over the first film layer to thereby form the multilayer structure for each of the plurality of data lines.

Specifically, the step S101 can be performed by several alternative patterning processes, which all result in the formation of the plurality of electrodes 01 and the first film layer 021 of each data line over the substrate, as illustrated in FIG. 5A.

Figure 6A:
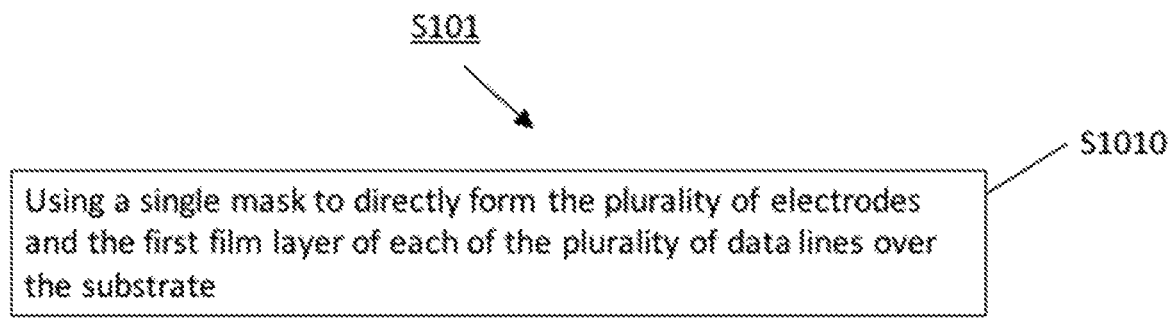
FIG. 6A and FIG. 6B respectively illustrates a flow chart of sub-step S101 during manufacturing of a data line of a sample testing apparatus according to two different embodiments of the present disclosure.

According to some embodiments, sub-step S101 may include a one-time patterning process, which can involve the use of a single mask having a specific pattern to directly form the plurality of electrodes 01 and the first film layer 021. As such, as illustrated in FIG. 6A, sub-step S101 specifically includes:

S1010: Using a single mask to directly form the plurality of electrodes 01 and the first film layer 021 of each of the plurality of data lines over the substrate.

Figure 6B:
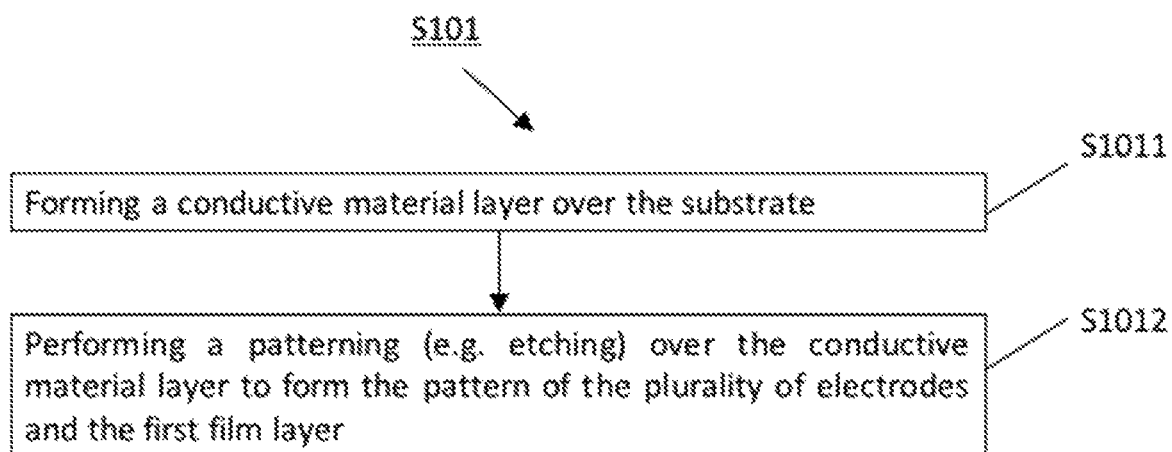

According to some other embodiments, sub-step S101 may include an etching process after the formation of a conductive material layer over the substrate. As such, as illustrated in FIG. 6B, sub-step S101 specifically includes the following two steps S1011 and S1012:

S1011: forming a conductive material layer over the substrate; and

S1012: performing an etching process over the conductive material layer to form the pattern of the plurality of electrodes 01 and the first film layer 021.

It is noted that besides the above two different patterning processes, it is possible the S101 can include other alternative fabrication processes.

Specifically, the step S102 can be performed by means of at least one patterning process over the substrate having the plurality of electrodes and the first film layer. The data line 02 having a multilayer structure after the step S102 according to some embodiments is illustrated in FIG. 5C.

Figure 7A:
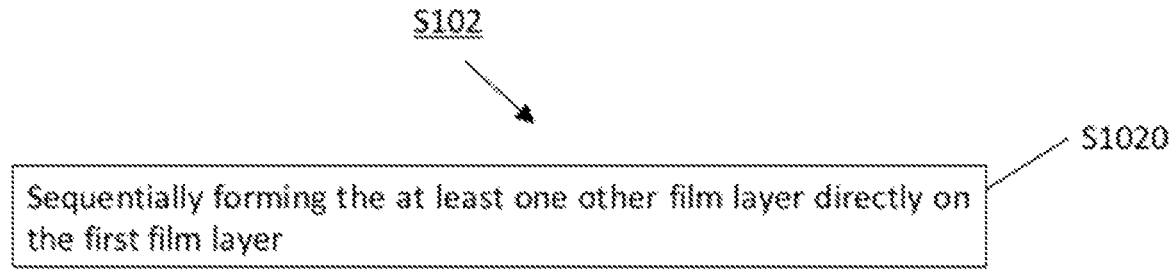
FIG. 7A and FIG. 7B respectively illustrates a flow chart of sub-step S102 during manufacturing of a data line of a sample testing apparatus according to two different embodiments of the present disclosure.

According to some embodiments of the manufacturing method, the multilayer structure for each data line comprises at least one other film layer over the first film layer and contains no insulating layers. As such, as illustrated in FIG. 7A, the step S102 comprises:

S1020: sequentially forming the at least one other film layer directly on the first film layer.

Herein the formation of each of the at least one other film layer in S1020 can be performed by a patterning process, such as a one-time patterning process using a single mask or a patterning process involving an etching process.

It is noted that in the sample testing apparatus manufactured by this above embodiment of the manufacturing method, there are at least two film layers that are directly stacked over one another (without the insulation layer having vias therebetween).

Figure 7B:
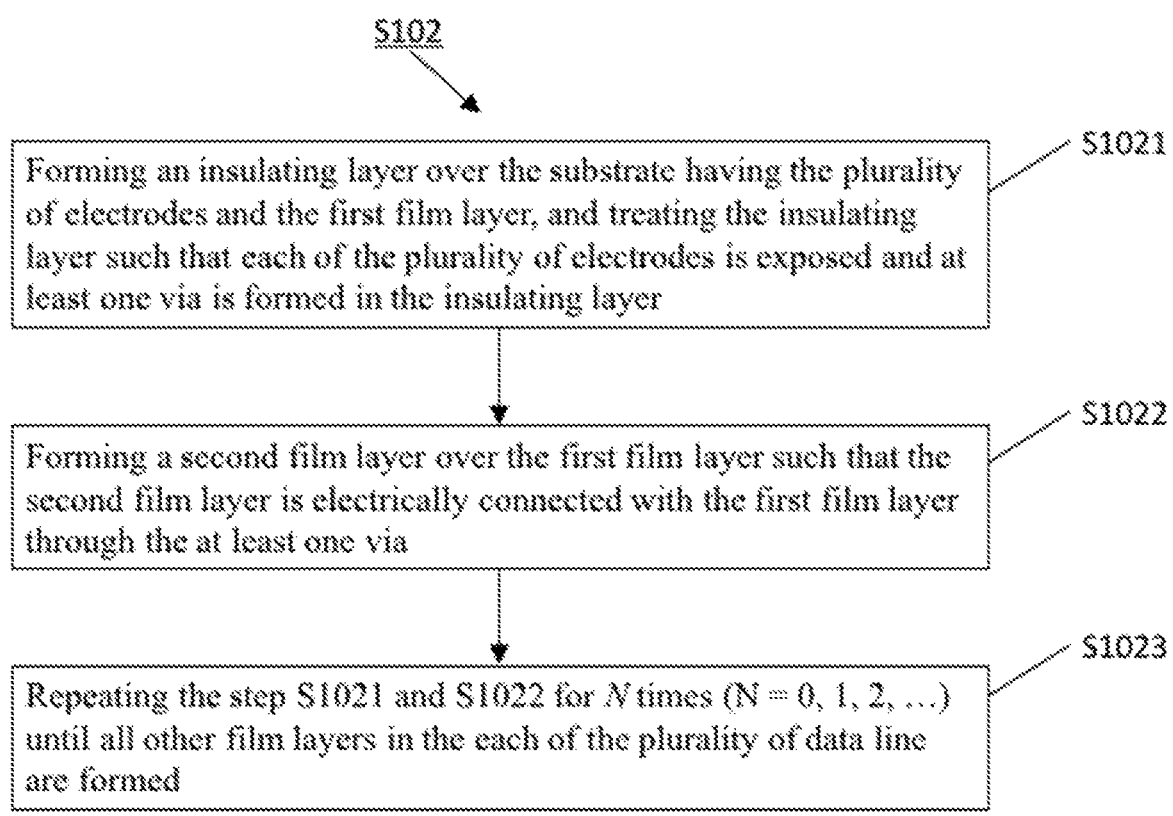

According to some other embodiments of the manufacturing method, the multilayer structure for each data line comprises an insulating layer, which is arranged between the first film layer and the at least one other film layer, and/or between two neighboring other film layers. As such, as illustrated in FIG. 7B, the step S102 can comprise the following sub-steps:

S1021: Forming an insulating layer 07 over the substrate having the plurality of electrodes 01 and the first film layer 021, and treating the insulating layer 07 such that each of the plurality of electrodes 01 is exposed and at least one via k is formed in the insulating layer 07.

Specifically, the exposure of the plurality of electrodes 01 and the formation of the at least one via k in the insulating layer 07 can be performed by using a single mask (i.e. a one-time mask etching process). The vias k are illustrated in FIG. 5B.

S1022: Forming a second film layer 022 over the first film layer 021 such that the second film layer 022 is electrically connected with the first film layer 021 through the at least one via k.

Specifically, the second film layer 022 can be formed by firstly forming a composition layer over the insulating layer having the at least one via k, and secondly performing a patterning over the composition layer to thereby form the second film layer 022. The patterning can be a one-time mask etching process, and the second film layer 022 formed is illustrated in FIG. 5C.

Optionally, the multilayer structure of each data line comprises two or more other film layers (i.e. second film layer, third film layer, etc., over the first film layer), which are insulated from one another by one insulating layer in between. As such, the sub-step S102 can further include:

S1023: repeating S1021 and S1022 for N times (N=0, 1, 2, . . . ) until all other film layers in the each of the plurality of data line are formed.

Specifically, each of the other film layers (i.e. a third film layer, a fourth film layer, etc.) in the data line can be formed by a patterning process as mentioned above (i.e. a one-time mask etching process for the second film layer 022), until the multilayer structure of the data line is formed.

It also noted that similar to the above mentioned sub-step S101 to form the plurality of electrodes 01 and the first film layer 021, at least one of the sub-steps (e.g. S201, S202, etc.) can also involve the fabrication process involving the formation of a material layer and a subsequent patterning (e.g. etching) over the material layer to thereby form the pattern of one specific layer (e.g. the insulating layer 07, the second film layer 022, etc.)

In the above mentioned method for manufacturing a sample testing apparatus, the step S100 of forming a plurality of detection devices over a substrate can further include sub-steps that substantially form each individual detection device of the sample testing apparatus.

Figure 8:
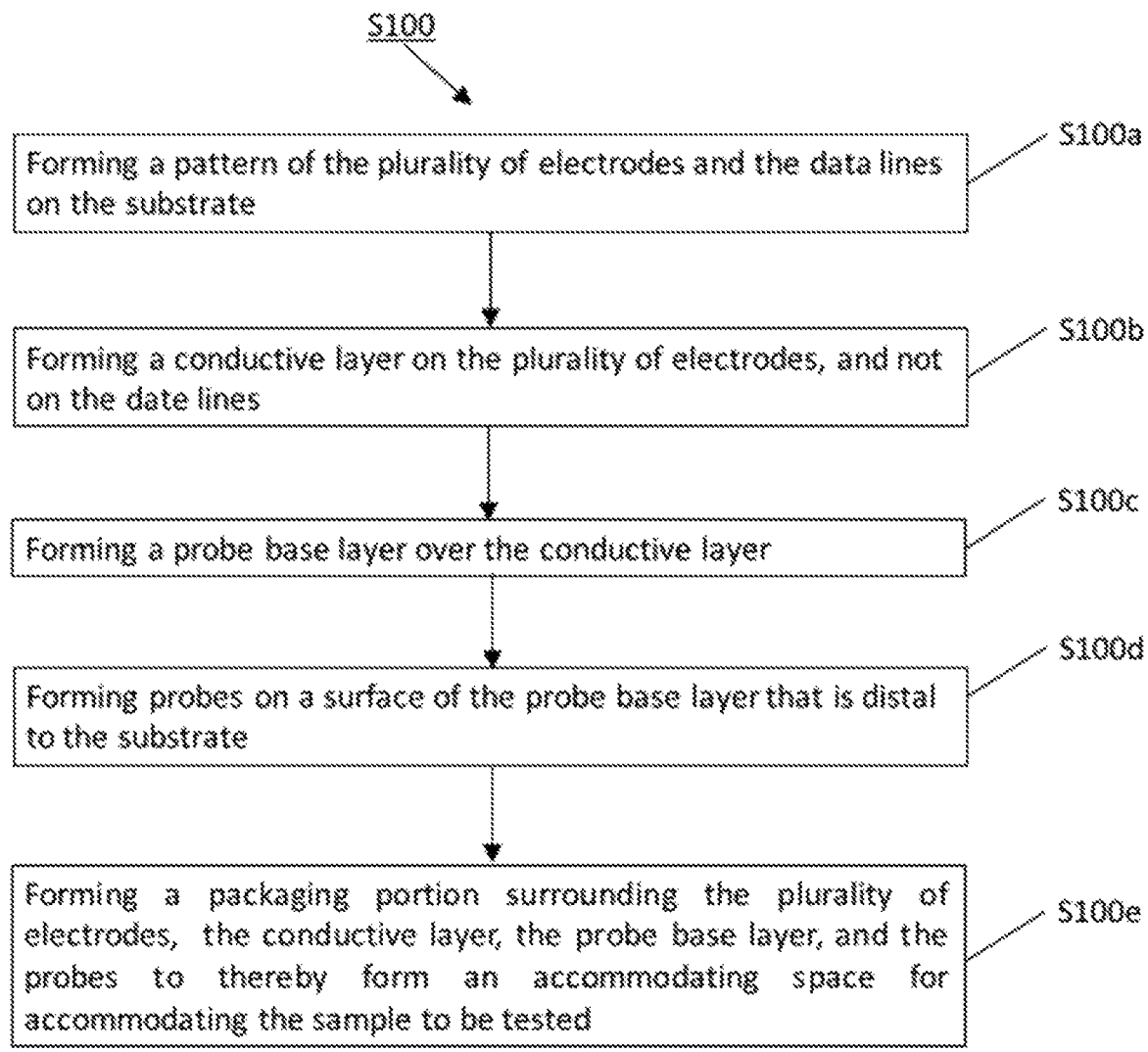
FIG. 8 illustrates a flow chart of forming detection devices of a sample testing apparatus according to some embodiments of the present disclosure.

According to some embodiment of the manufacturing method which substantially results in the detection device having a structure as illustrated in FIG. 3B (i.e. each of the conductive layer 03 and the probe base layer 04 is an integrated structure), the step S100 of forming a plurality of detection devices over a substrate substantially include the following sub-steps, as illustrated in FIG. 8. The intermediate product after each of the above sub-steps is respectively illustrated in FIGS. 9A-9E.

Figure 9A:
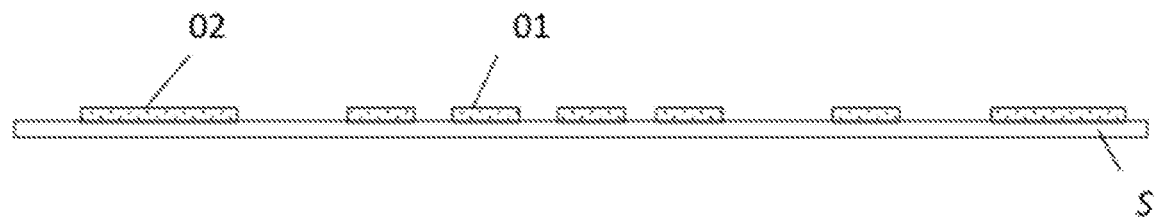
FIG. 9A, FIG. 9B, FIG. 9C, FIG. 9D, and FIG. 9E respectively show a schematic diagram of an intermediate product of a detection device after each fabrication step as shown in FIG. 8.
Figure 9B:
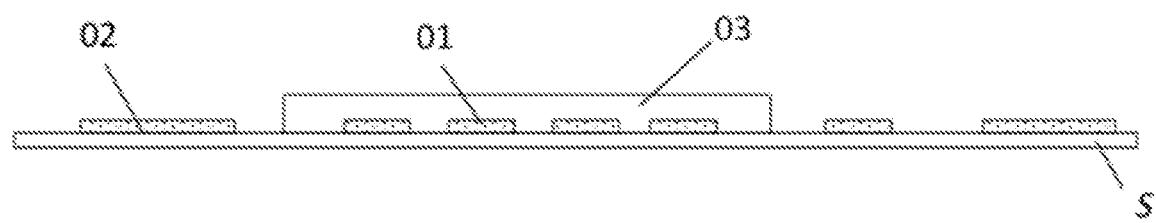
Figure 9C:
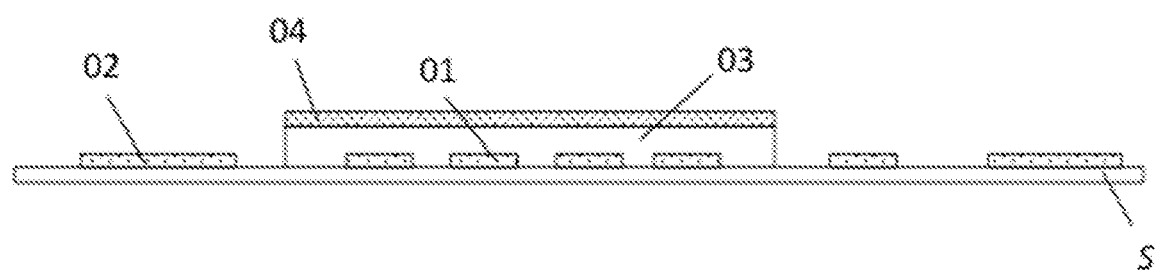
Figure 9D:
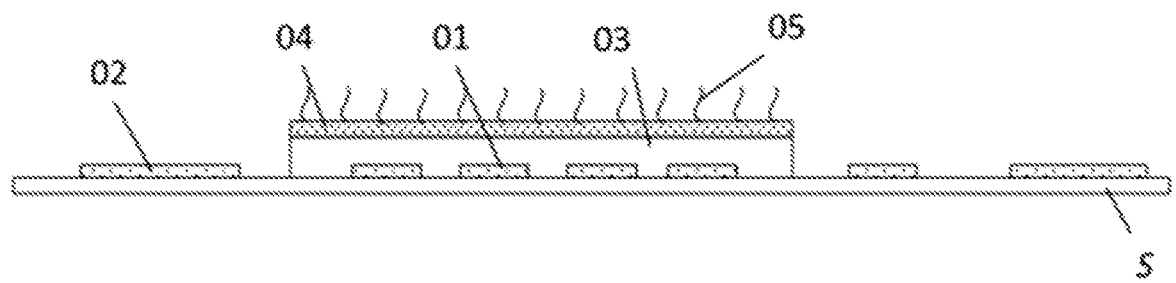
Figure 9E:
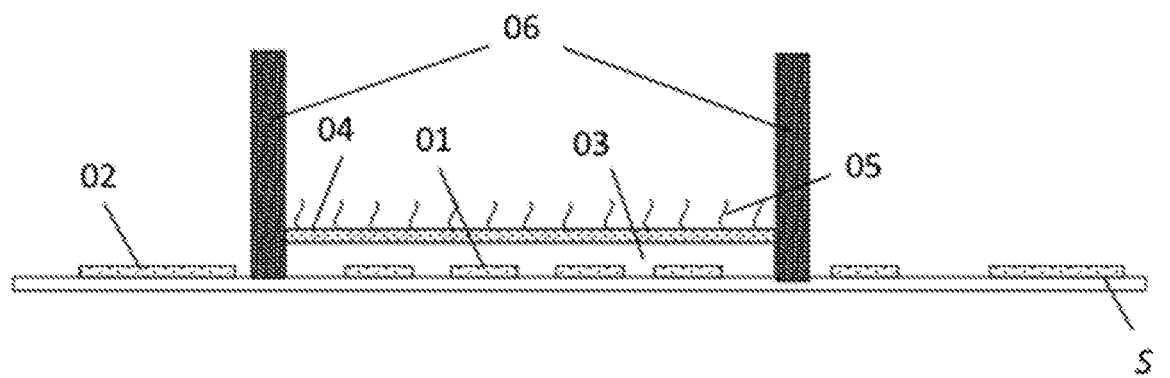

As shown in FIG. 8, the step S100 of forming a detection device over a substrate includes:

S100a: Forming a pattern of the plurality of electrodes 01 and the data lines 02 on the substrate S (the intermediate product after S100a is shown in FIG. 9A);

S100b: Forming a conductive layer 03 on the plurality of electrodes 01, and not on the data lines 02 (the intermediate product after S100b is shown in FIG. 9B);

S100c: Forming a probe base layer 04 over the conductive layer 03 (the intermediate product after S100c is shown in FIG. 9C);

S100d: Forming probes 05 on a surface of the probe base layer 04 that is distal to the substrate (the intermediate product after S100d is shown in FIG. 9D); and S100e: Forming packaging portion 06 surrounding the plurality of electrodes 01, the conductive layer 03, the probe base layer 04, and the probes 05 to thereby form an accommodating space for accommodating the sample to be tested (the intermediate product after S100e is shown in FIG. 9E).

Figure 10:
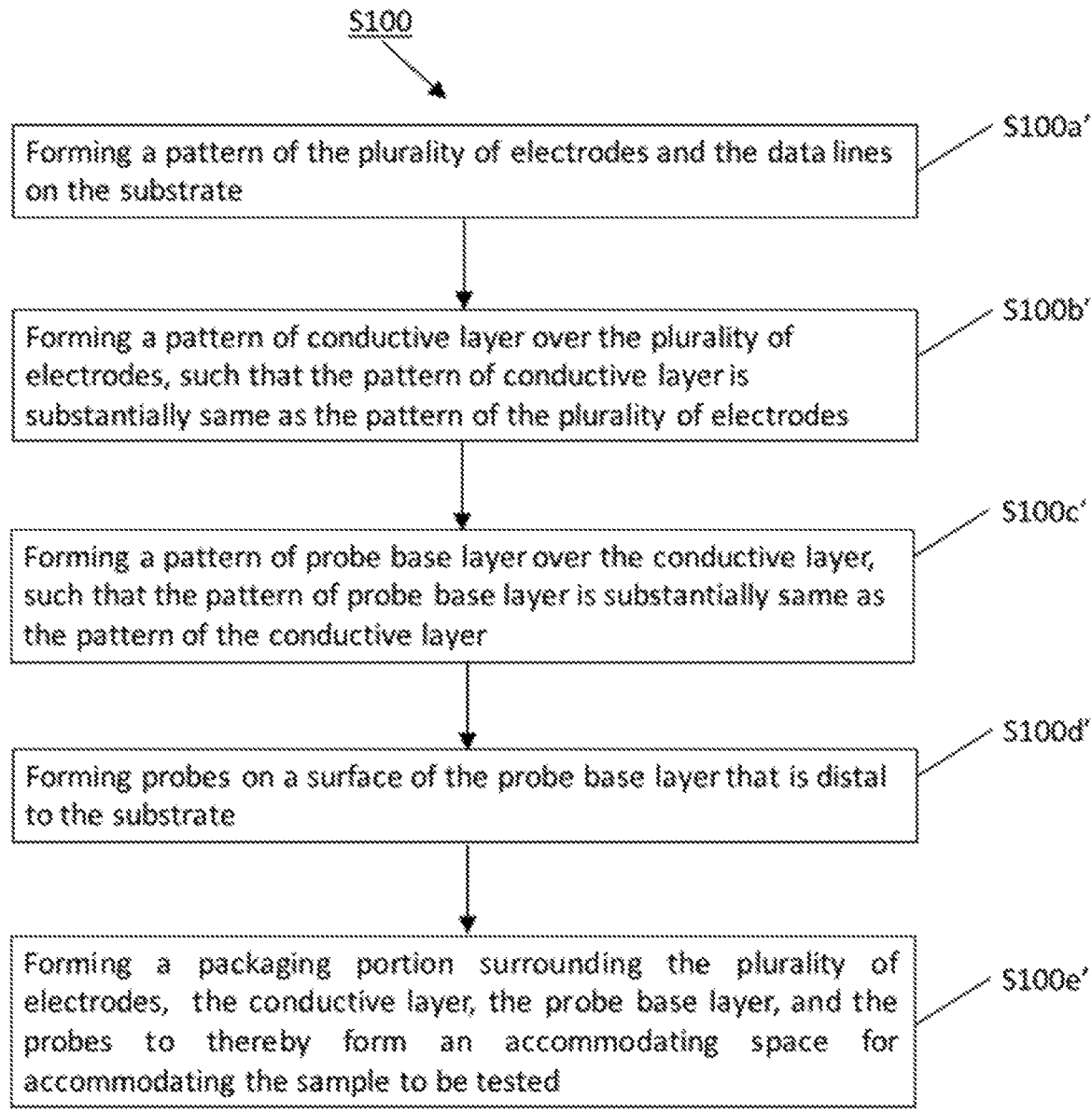
FIG. 10 illustrates a flow chart of forming detection devices of a sample testing apparatus according to some other embodiments of the present disclosure.

According to some other embodiments of the manufacturing method which substantially results in the detection device having a structure as illustrated in FIG. 3A (i.e. each of the conductive layer 03 and the probe base layer 04 has a pattern that is substantially same as the pattern of the plurality of electrodes 01), the step S100 of forming a plurality of detection devices over a substrate substantially include the following sub-steps, as illustrated in FIG. 10.

S100a': Forming a pattern of the plurality of electrodes 01 and the data lines 02 on the substrate S;

S100b': Forming a pattern of conductive layer 03 over the plurality of electrodes 01, such that the pattern of conductive layer 03 is substantially same as the pattern of the plurality of electrodes 01;

S100c': Forming a pattern of probe base layer 04 over the conductive layer 03, such that the pattern of probe base layer 04 is substantially same as the pattern of the conductive layer 03;

S100d': Forming probes 05 on a surface of the probe base layer 04 that is distal to the substrate; and S100e': Forming packaging portion 06 surrounding the plurality of electrodes 01, the conductive layer 03, the probe base layer 04, and the probes 05 to thereby form an accommodating space for accommodating the sample to be tested.

It is noted in any of the sub-steps S100a (i.e. formation of the pattern of conductive layer 03) and S100b (i.e. formation of the pattern of probe base layer 04) can be realized by a one-time patterning process (i.e. use of a single mask), or by a multi-step process, involving a step of formatting a material layer (i.e. a layer of composition for the conductive layer 03 or a layer of composition for the probe base layer 04) and a step of etching the material layer to thereby form the pattern of the conductive layer 03 and/or the pattern of the probe base layer 04.

In a third aspect, the disclosure provides a method for sample testing using the sample testing apparatus as mentioned above.

Figure 11:
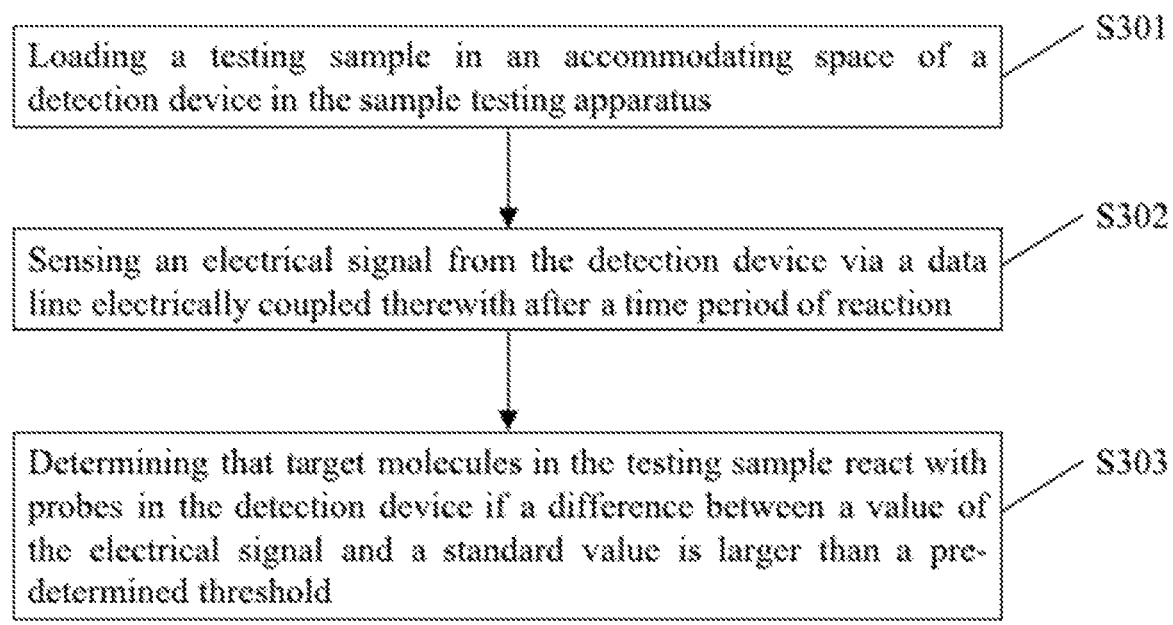
FIG. 11 illustrates a flow chart of a sample testing method utilizing the sample testing apparatus disclosed herein according to some embodiments of the present disclosure.

FIG. 11 illustrates a flow chart of a sample testing method utilizing the sample testing apparatus disclosed herein according to some embodiments of the present disclosure. As shown in FIG. 11, the sample testing method comprises:

S301: Loading a testing sample in the accommodating space of the detection device in the sample testing apparatus;

S302: Sensing an electrical signal from the detection device via the data line electrically coupled therewith after a time period of reaction; and S303: Determining that target molecules in the testing sample react with probes in the detection device if a difference between a value of the electrical signal and a standard value is larger than a pre-determined threshold.

The sample testing method utilizing the aforementioned sample testing apparatus have an advantages such as simplicity and low testing noises.

Together, the present disclosure provides a sample testing apparatus, its manufacturing method, and a sample testing method using the sample testing apparatus. The sample testing apparatus includes a plurality of detection devices over a substrate. Each detection device comprises a plurality of electrodes and a plurality of data lines.

Each data line is a multilayer structure and comprises a plurality of film layers. A first film layer in each data line is at a substantially same layer as the plurality of electrodes and has a first composition that is substantially same as the conductive material used for the plurality of electrodes. Other film layers in each data line comprises at least one second film layer having a composition that has a relatively lower electric resistance than the first film layer.

As such, in each of the plurality of data lines having the above mentioned multilayer structure, the first film layer in each data line can be configured to be at a substantially same layer and have a substantially same composition as the plurality of electrodes. The composition for the electrodes and the first film layer of each data line is configured to have a relatively good compatibility to target molecules in the sample, and to have a relatively high electric resistance, and the composition for other film layers of each data line is configured to have a relatively low electric resistance. Thereby, the sample testing apparatus has the following advantageous features: first, the electrodes have a good compatibility with the sample; and second, the data lines have relatively low electric resistance. As such, the testing noise during sample testing can be effectively reduced.

Although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A sample testing apparatus for characterizing at least one target molecule in a testing sample, comprising:
   a substrate; and
   at least one detection device over the substrate, each comprising:
      an accommodating space formed within a packaging portion, the packaging portion extending perpendicular from the substrate;
      a plurality of data lines, each of the plurality of data lines comprising a first film layer abutting the substrate and a second film layer on an opposite side of the first film layer from the substrate;
      a plurality of electrodes abutting the substrate within the accommodating space, the plurality of electrodes being formed from a common layer as the first film layer such that electrical resistance of the data lines are reduced and the plurality of probes have improved compatibilities with the testing sample; and
      a probe extending away from the substrate within the accommodating space, the probe configured to react with one of the at least one target molecule;
   wherein:
      each of the plurality of electrodes is electrically coupled to one of the plurality of data lines;
      each of the plurality of electrodes is configured, upon reaction of the probe with the one of the at least one target molecule, to sense an electrical signal, and then to transmit the electrical signal via the one of the plurality of data lines;
      the first film layer extends along the substrate from outside the accommodating space to inside the accommodating space;
      the first film layer has a first composition;
      the second film layer has a second composition;
      the second composition has an electrical resistance lower than an electrical resistance of the first composition; and
      the at least one detection device over the substrate each further comprises:
         a conductive layer disposed over the plurality of electrodes; and
         a probe base layer disposed over the conductive layer and configured to provide a surface for attaching or growing the probe to specifically react with the one of the at least one target molecule.

2. The sample testing apparatus of claim 1, wherein in each of the at least one detection device, the plurality of electrodes are grouped into at least one subset of electrodes, wherein:
   each of the at least one subset of electrodes are electrically coupled to a same data line.

3. The sample testing apparatus of claim 2, wherein in each of the at least one detection device,
   the plurality of data lines comprise a first data line and a second data line; and
   the plurality of electrodes are grouped into two subsets of electrodes, electrically coupled to the first data line and the second data line respectively.

4. The sample testing apparatus of claim 3, wherein in each of the at least one detection device, the plurality of electrodes are arranged in a matrix having a plurality of rows, wherein:
   electrodes in each of the plurality of rows are connected to one another in series;
   one of the two subsets of electrodes comprises electrodes in odd-number rows; and
   another of the two subsets of electrodes comprises electrodes in even-number rows.

5. The sample testing apparatus of claim 1, wherein the packaging portion encircles the plurality of electrodes and the testing sample.

6. The sample testing apparatus of claim 5, wherein each of the at least one detection device further comprises, within the accommodation space:
   a conductive layer over a side of the plurality of electrodes distal to the substrate; and a probe base layer over a side of the conductive layer distal to the substrate, configured to provide a surface for attaching or growing molecules of the probe thereon.

7. The sample testing apparatus of claim 6, wherein each of the conductive layer and the probe base layer is formed having a common pattern with the plurality of electrodes.

8. A method for manufacturing the sample testing apparatus of claim 1, comprising:
providing the substrate; and
forming the at least one detection device over the substrate.

9. The method according to claim 8, wherein the forming at least one detection device over the substrate comprises:
forming the plurality of electrodes and the first film layer of each of the plurality of data lines over the substrate; and
forming the at second film layer of the each of the plurality of data lines over a side of the first film layer distal to the substrate.

10. The method according to claim 9, wherein the forming the plurality of electrodes and the first film layer of each of the plurality of data lines over the substrate is performed by using a single mask.

11. The method according to claim 9, wherein the forming at least one detection device over the substrate further comprises:
forming a conductive layer over a side of the plurality of electrodes distal to the substrate;
forming a probe base layer over a side of the conductive layer distal to the substrate; and
forming the probe on a surface of the probe base layer distal to the substrate.

12. The method according to claim 11, wherein the package portion encircles the plurality of electrodes to thereby form an accommodation space for the testing sample.

* * * * *